US012111001B2

(12) United States Patent
Cassiday et al.

(10) Patent No.: US 12,111,001 B2
(45) Date of Patent: Oct. 8, 2024

(54) FLUID TRANSPORT COUPLING

(71) Applicant: SAINT-GOBAIN PERFORMANCE PLASTICS CORPORATION, Solon, OH (US)

(72) Inventors: Bryan L. Cassiday, Beaverton, MI (US); Mitchell L. Snyder, Hope, MI (US); Nicolas Nadenoff, Beaverton, MI (US); Thomas R. Nixon, Au Gres, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 356 days.

(21) Appl. No.: 15/374,857

(22) Filed: Dec. 9, 2016

(65) Prior Publication Data

US 2017/0167652 A1    Jun. 15, 2017

Related U.S. Application Data

(60) Provisional application No. 62/265,861, filed on Dec. 10, 2015.

(51) Int. Cl.
*F16L 37/56* (2006.01)
*A61M 39/10* (2006.01)
*F16L 39/00* (2006.01)

(52) U.S. Cl.
CPC ........... *F16L 37/56* (2013.01); *A61M 39/105* (2013.01); *F16L 39/00* (2013.01); *F16L 2201/44* (2013.01)

(58) Field of Classification Search
CPC ....... F16L 37/56; F16L 39/00; F16L 2201/44; F16L 41/02; F16L 41/03; F16L 55/0263; F16L 11/22; A61M 39/105

USPC .......... 285/124.5, 120.1, 123.1, 123.2, 124.1
See application file for complete search history.

(56) References Cited

U.S. PATENT DOCUMENTS

| 3,214,194 | A | * | 10/1965 | Gostling | |
|---|---|---|---|---|---|
| 3,214,195 | A | * | 10/1965 | Zahuranec | F16L 37/23 |
| | | | | | 285/124.1 |
| 3,332,566 | A | * | 7/1967 | Phillips | |

(Continued)

FOREIGN PATENT DOCUMENTS

| EP | 0738852 A1 | 10/1996 |
|---|---|---|
| EP | 2805737 A1 | 11/2014 |
| WO | 2017100672 A1 | 6/2017 |

OTHER PUBLICATIONS

International Search Report for PCT/US2016/065971, mailed Apr. 7, 2017, 1 page.

(Continued)

*Primary Examiner* — William S. Choi
(74) *Attorney, Agent, or Firm* — Abel Schillinger, LLP; Chi Suk Kim

(57) ABSTRACT

A sanitary fluid transport coupling can include a plurality of fluid conduits, each fluid conduit having a distal end and a proximal end, a support element adapted to secure a spaced relationship between the plurality of second conduits at the distal end of the plurality of fluid conduits, and an overmolded element disposed adjacent the support element. The overmolded element can form a fitting that can form a fluid connection with another fluid conduit, fluid container, or isolated environment.

22 Claims, 4 Drawing Sheets

(56) References Cited

U.S. PATENT DOCUMENTS

| | | | | |
|---|---|---|---|---|
| 3,747,632 | A * | 7/1973 | Kok | B29C 44/18 |
| | | | | 137/375 |
| 4,226,368 | A * | 10/1980 | Hunter | 239/542 |
| 4,613,080 | A * | 9/1986 | Benson | 138/45 |
| 4,703,957 | A * | 11/1987 | Blenkush | F16L 37/56 |
| | | | | 285/239 |
| 4,722,559 | A * | 2/1988 | Bongartz | |
| 4,754,993 | A * | 7/1988 | Kraynick | F16L 37/56 |
| 5,157,642 | A * | 10/1992 | Tsukamura | 369/30.15 |
| 5,236,227 | A | 8/1993 | Adams et al. | |
| 5,607,190 | A † | 3/1997 | Exandier | |
| 5,943,711 | A * | 8/1999 | Loizeaux | |
| 6,290,265 | B1 | 9/2001 | Warburton-Pitt et al. | |
| 6,692,037 | B1 * | 2/2004 | Lin | 285/124.1 |
| 6,966,581 | B2 † | 11/2005 | Mastropaolo | |
| 7,407,612 | B2 † | 8/2008 | Warburton-Pitt | |
| 7,578,205 | B2 | 8/2009 | Belongia | |
| 7,584,675 | B2 | 9/2009 | Evans | |
| 7,766,043 | B2 * | 8/2010 | Thomas | |
| 7,921,740 | B2 | 4/2011 | Furey et al. | |
| 8,469,056 | B2 * | 6/2013 | Marty | 137/625.4 |
| 8,505,396 | B2 | 8/2013 | Zumbrum | |
| 8,613,422 | B2 | 12/2013 | Zumbrum | |
| 8,957,778 | B2 | 2/2015 | Adams et al. | |
| 9,320,867 | B2 | 4/2016 | Yeomans et al. | |
| 2004/0232696 | A1 † | 11/2004 | Andre | |
| 2005/0256461 | A1 | 11/2005 | Difiore et al. | |
| 2009/0051164 | A1 | 2/2009 | Lirsch et al. | |
| 2010/0290764 | A1 † | 11/2010 | Borgmeier | |
| 2011/0210547 | A1 * | 9/2011 | Ryall | |
| 2011/0275945 | A1 | 11/2011 | Karla et al. | |
| 2012/0223517 | A1 | 9/2012 | Morrissey et al. | |
| 2013/0106060 | A1 * | 5/2013 | Beele | |
| 2013/0144234 | A1 | 6/2013 | Croizat et al. | |
| 2013/0263936 | A1 * | 10/2013 | DeVries | |
| 2013/0304039 | A1 | 11/2013 | Chung | |
| 2014/0261747 | A1 * | 9/2014 | Bares | 137/15.21 |
| 2016/0146392 | A1 † | 5/2016 | Pennock | |
| 2016/0195208 | A1 † | 7/2016 | Cassiday | |
| 2016/0305582 | A1 † | 10/2016 | Blomberg | |
| 2016/0368192 | A1 † | 12/2016 | Seman | |
| 2017/0114559 | A1 * | 4/2017 | Scatterday | |

OTHER PUBLICATIONS

Supplementary European Search Report for EP16873986, completed Jul. 10, 2019, 7 pages.
Lin Mei et al., High School Chemistry Training and Question Bank, China Civil Aviation Publishing House, Dec. 31, 1997, pp. 49-51.

* cited by examiner
† cited by third party

FLUID TRANSPORT COUPLING

CROSS-REFERENCE TO RELATED APPLICATION(S)

This application claims priority under 35 U.S.C. § 119(e) to U.S. Patent Application No. 62/265861 entitled "FLUID TRANSPORT COUPLING," by Mitchell L. Snyder, Bryan L. Cassiday, Nicolas Nadenoff, and Thomas R. Nixon, filed Dec. 10, 2015, which is assigned to Saint-Gobain Performance Plastics Corporation hereof and incorporated herein by reference in its entirety.

FIELD OF THE DISCLOSURE

The present disclosure relates to fluid transport couplings, and more particularly to, fluid transport couplings transitioning flow to a plurality of fluid conduits.

BACKGROUND

Large-scale production of pharmaceuticals, fluids for use in medical applications, and food grade products relies on maintenance of sanitary environments. Exposure of such products to bacteria or contaminants results in a reduced quality and, in some cases, toxic byproducts. As such, food and medical product manufacturers attempt to reduce points of contamination and have turned to sanitary hoses and connectors as part of an effort to maintain a sanitary environment. There exists a need for improved sanitary hoses and connectors.

BRIEF DESCRIPTION OF THE DRAWINGS

Embodiments are illustrated by way of example and are not limited in the accompanying figures.

Figure 1:
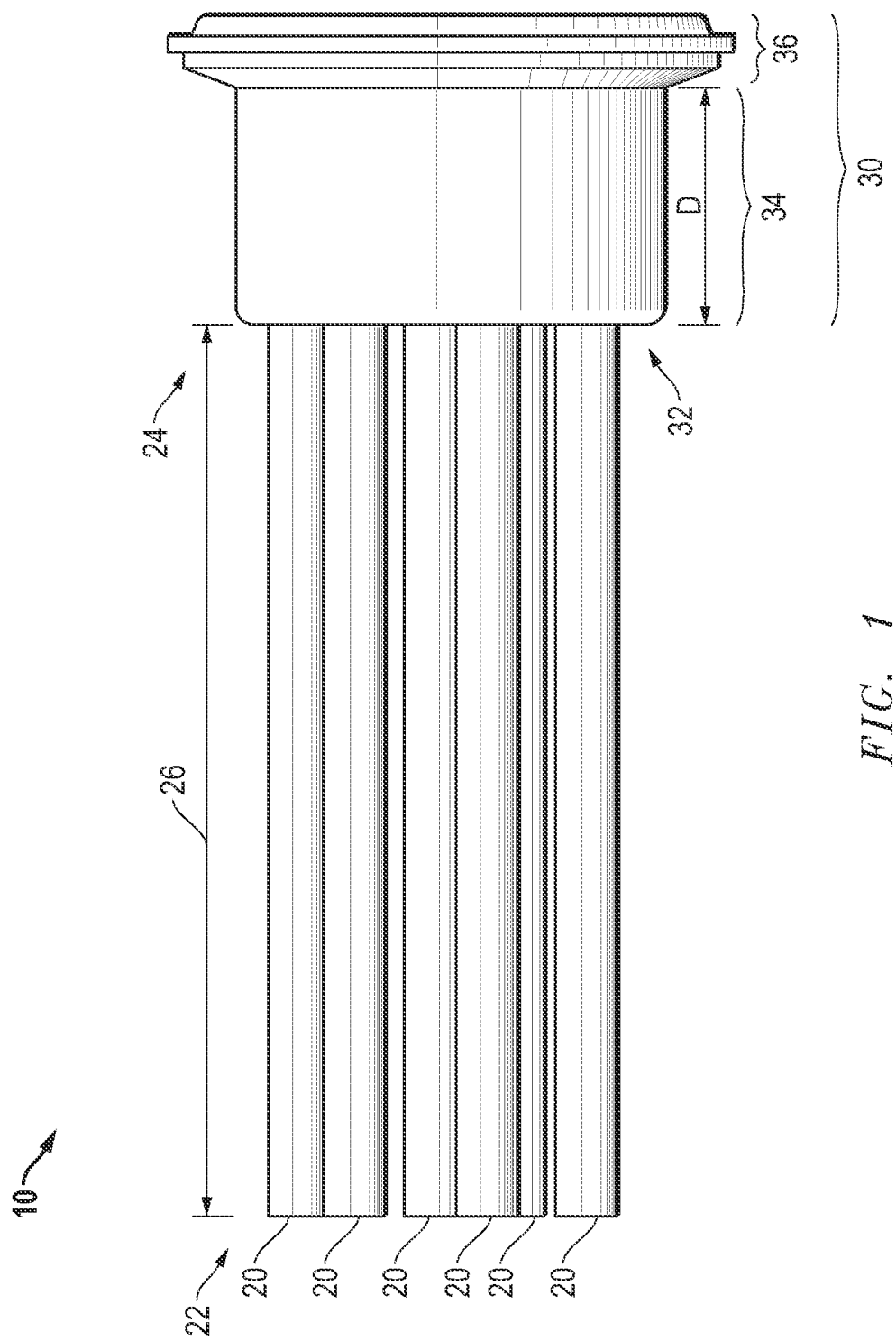
FIG. 1 includes an illustration of a side view of a multi-port fluid transport coupling according to one embodiment.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the fluid transport arts.

The present disclosure is directed to fluid transport coupling elements that can provide a more robust fluid connection and methods of forming fluid transport couplings that can greatly improve their manufacture. Fluid transport couplings function to transport fluid to or from a fluid conduit or between fluid conduits. For example, sanitary fluid transport couplings can be used to join pipes, valves, and fittings in the food, dairy, beverage, pharmaceutical, and life sciences industries.

A particular advantage of certain embodiments of the present disclosure is the ability to form and secure a fluid connection between a plurality of fluid conduits simultaneously. Previously, a fluid connection between a plurality of fluid conduits required separately-formed fluid connections with a fluid connecting element for each individual fluid conduit. By contrast, embodiments of the present disclosure include a single overmolding step that forms a fluid connection between a plurality of fluid conduits simultaneously and with the same fluid connector. For example, as disclosed herein, a fluid connector can be formed onto the fluid conduits via overmolding. The concepts are better understood in view of the embodiments described below that illustrate and do not limit the scope of the present invention.

Referring now to FIG. 1, a fluid transport coupling 10 can include first fluid conduits 20, each first fluid conduit having a distal end 22 and a proximal end 24, and a fluid connector 30 disposed adjacent the proximal ends of the first fluid conduits 20. The fluid connector 30 can have a body 34 and a connecting end 32, where the connecting end 32 is the end farthest from the distal end 22 of the fluid conduits 20.

Figure 2:
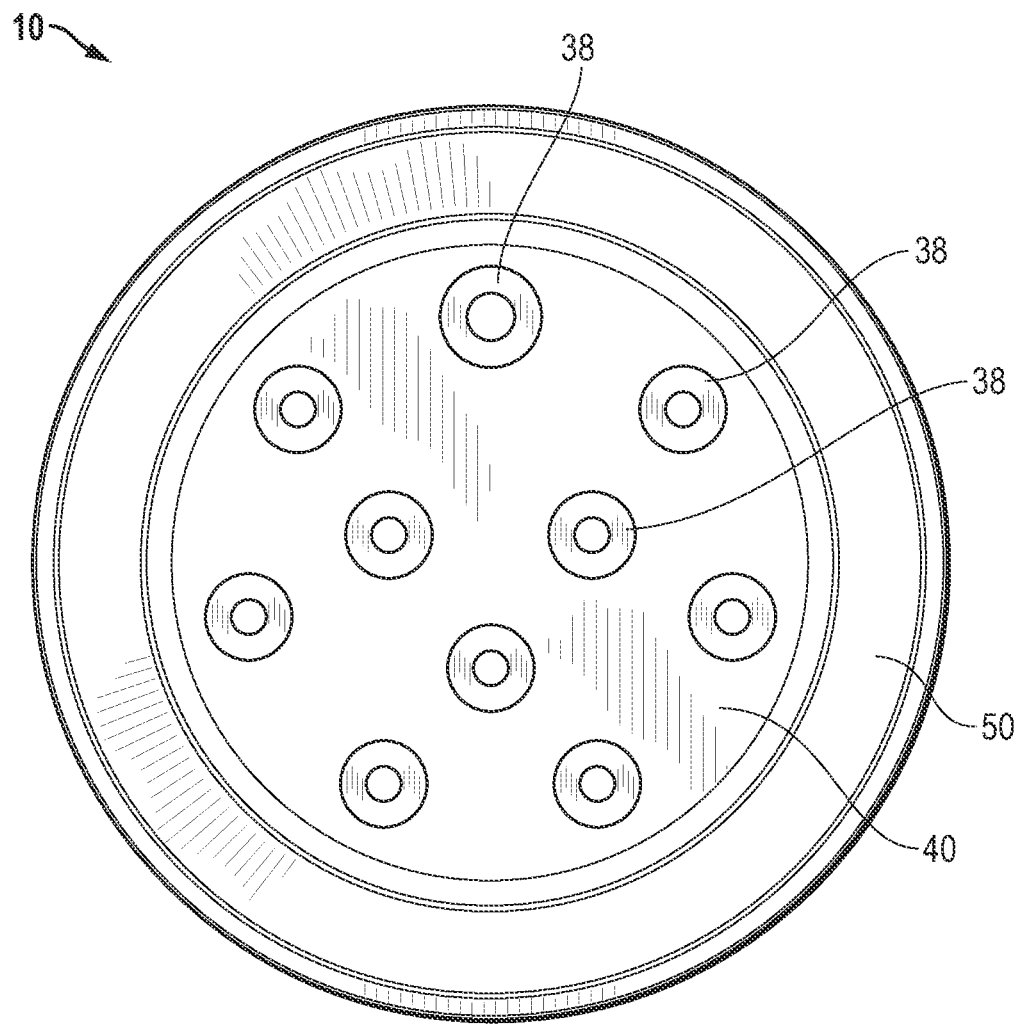
FIG. 2 includes an illustration of an end view of a multi-port fluid transport coupling according to one embodiment.
Figure 3:
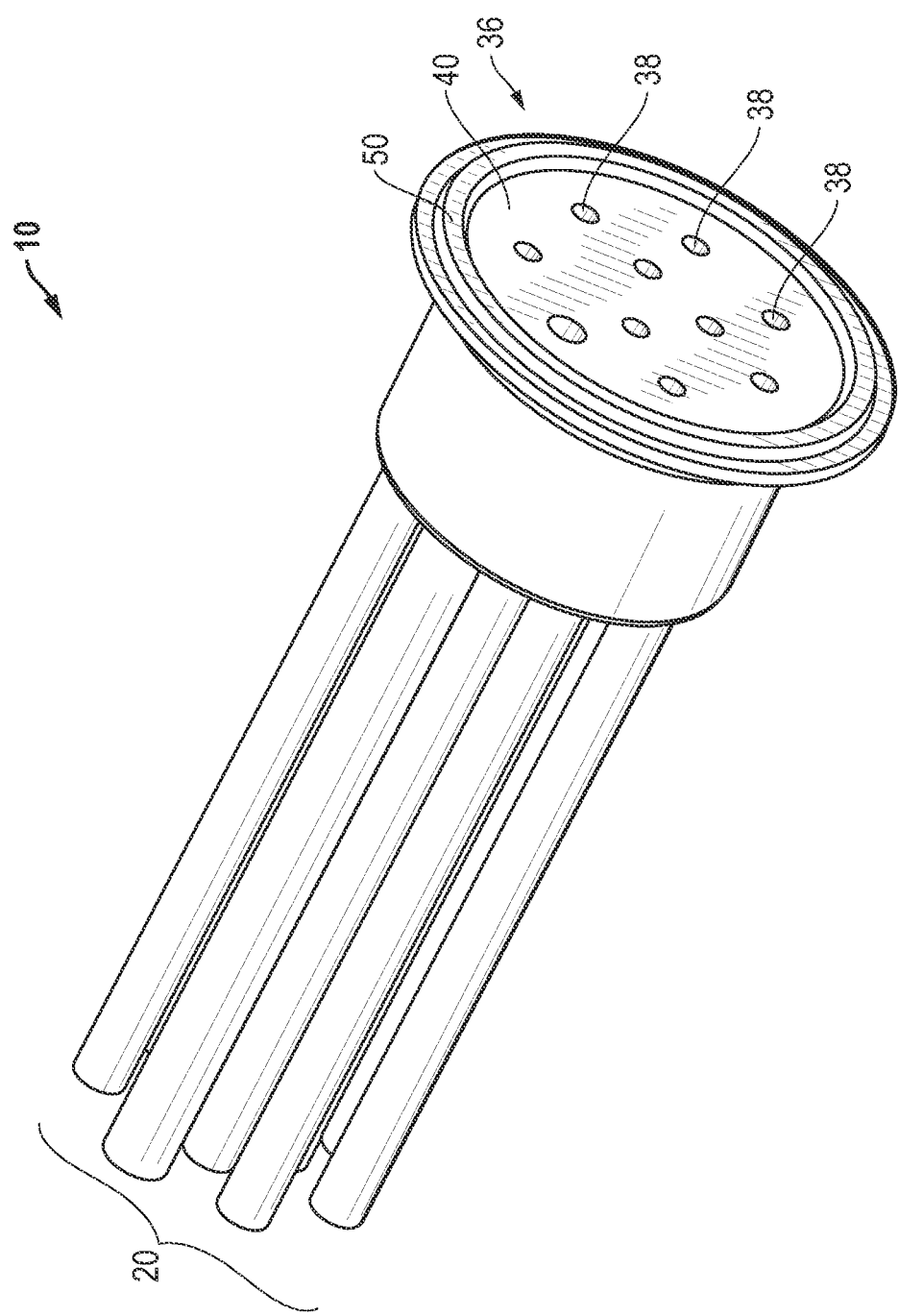
FIG. 3 includes an illustration of a first perspective view of a multi-port fluid transport coupling according to one embodiment.
Figure 4:
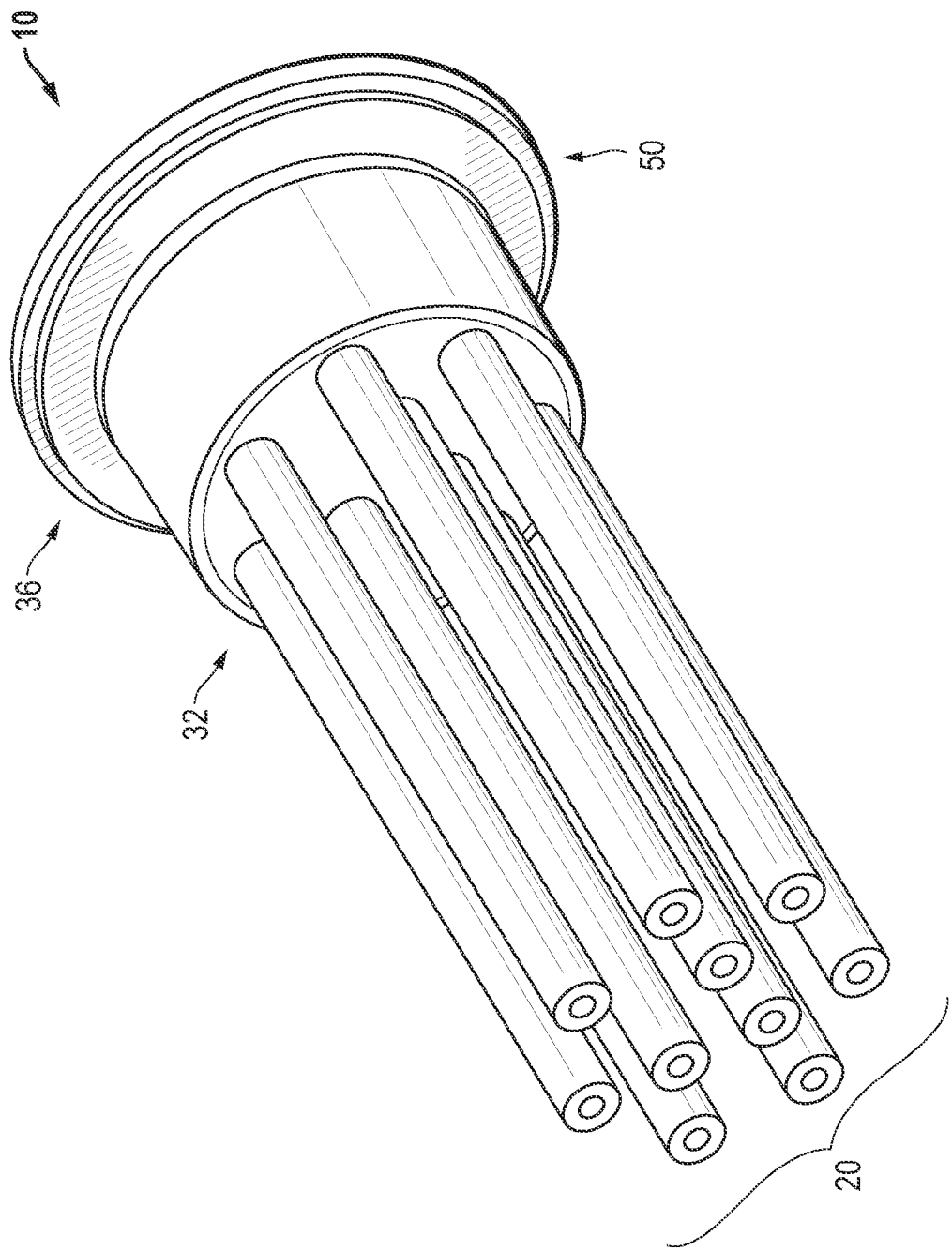
FIG. 4 includes an illustration of a second perspective view of a multi-port fluid transport coupling according to one embodiment.

Further, referring to FIG. 2, the fluid connector 30 can be a composite comprising a support element 40 and a connector element 50 overmolded onto the support element. The support element 40 can be adapted to arrange and secure a spaced relationship between the first fluid conduits 20, and the connector element 50 can be disposed over the support element to sure a fluid connection between the fluid conduits 20 and the connecting end 12 of the fluid transport coupling 10. Furthermore, as will be discussed in more detail later in the application, the fluid connector 30 can be formed by overmolding the connector element material about both the support element 40 and the proximal ends 24 of the fluid conduits 20 to secure the fluid connection. In other words, the connector element 50 can be an overmolded connector element.

As discussed above, the fluid conduits 20 can each have a distal end 22, a proximal end 24, and a length 26 extending from the distal end 22 to the proximal end 24. In certain embodiments, the fluid conduits 20 can include inner and outer diameter profiles that are concentric and congruous. However, the profiles of the inner and outer diameters of the fluid conduits 20 can vary depending on the desired application.

In certain embodiments, the fluid conduits 20 can be composed of a flexible material. As used herein, the term "flexible material" refers to a material that is capable of undergoing strain, such as bending or stretching, without adverse impact of physical characteristics, such as irreversible break-down associated with material fracture, for example.

In certain embodiments, the flexible material can include a polymer, such as an elastomeric polymer. In particular embodiments, the elastomeric polymer can comprise an ether, an olefin, a vinyl, a polyurethane, an acrylate, a vinyl alcohol, an ethylene copolymer, an ester, a silicone, a fluoropolymer, or any combination thereof. In particular embodiments, the flexible material can include a silicone or a thermoplastic elastomer. In particular embodiments, one or more of the plurality of fluid conduits 20 can include an elastomeric polymer comprising a silicone.

One or more of the fluid conduits 20 can be made from the same material or made from a different material. In particular embodiments, each of the fluid conduits 20 can be made from the same material. In more particular embodiments, each of the fluid conduits 20 can include an elastomeric polymer comprising a silicone, such as include the same elastomeric polymer comprising a silicone.

The fluid transport coupling 10 can include at least 2, at least 3, at least 4, at least 5, at least 6, at least 7, at least 8, at least 9, or even at least 10 distinct fluid conduits 20. The conduits are distinct in that they are separated from each other prior to forming the fluid transport coupling 10, such as prior to any overmolding step of forming the connector 30 about the fluid conduits 20. In some embodiments, the plurality of fluid conduits 20 may include no greater than 15, no greater than 14, no greater than 13, no greater than 12, no greater than 11, or even no greater than 10 distinct fluid conduits. In further embodiments, the plurality of fluid conduits 20 can include a number of distinct fluid conduits in a range of 2 to 15, 5 to 14, or even 7 to 13 distinct fluid conduits. The number of fluid conduits 20 in the fluid transport coupling 10 can vary depending on the application, and can include more or less than the numbers listed above.

The size of fluid conduits 20 can vary as a group or within the group of fluid conduits, depending on the application. In certain embodiments, each of the fluid conduits 20 can have essentially the same inner diameter, essentially the same outer diameter, essentially the same length, or any combination thereof. In particular embodiments, each of the fluid conduits 20 can have essentially the same inner diameter. In more particular embodiments, each of the fluid conduits 20 can have essentially the same outer diameter. In more particular embodiments, each of the fluid conduits 20 can have essentially the same length.

In further embodiments, at least two of the fluid conduits 20 can have a different inner diameter, a different outer diameter, a different length, or any combination thereof. In particular embodiments, at least two of the fluid conduits 20 can have a different inner diameter. In more particular embodiments, at least two of the fluid conduits 20 can have a different outer diameter. In more particular embodiments, at least two of the fluid conduits 20 can have a different length.

In certain embodiments, the inner diameter of the fluid conduits 20 can be at least 0.01 cm, at least 0.02 cm, at least 0.03 cm, at least 0.04 cm, or even at least 0.05 cm. In further embodiments, the inner diameter can be no greater than 5 cm, no greater than 4 cm, no greater than 3 cm, no greater than 2 cm, or even no greater than 1.5 cm. Moreover, the inner diameter of the fluid conduits 20 can be greater than or less than the above values depending on the desired application.

In certain embodiments, the outer diameter of the fluid conduits 20 can be at least 0.05 cm, at least 0.07 cm, at least 0.09 cm, at least 0.11 cm, at least 0.13 cm, or even at least 0.15 cm. In further embodiments, the outer diameter can be no greater than 6 cm, no greater than 5 cm, no greater than 4 cm, no greater than 3 cm, or even no greater than 2 cm. Moreover, the outer diameter of the fluid conduits 20 can be greater than or less than the above values depending on the desired application.

In certain embodiments, the length of the fluid conduits 20 can be at least 5 cm. However, the length can be less than 5 cm depending on the desired application.

The fluid connector 30 can form a fluid connection with the fluid conduits 20. As discussed above, the fluid connector 30 can be disposed at the proximal ends 24 of the fluid conduits 20. As will be discussed in more detail later in the application, the fluid connector 30 can also form a fluid connection with a fluid component to, for example, transport fluid to, from, or between the fluid conduits 20 and the fluid component.

The shape and size of the fluid connector 30 can vary depending on the application in which the fluid transport coupling 10 is used. The fluid connector can include a body end 32, a body 34, a connecting end 36, and ports 38 (see FIG. 2) extending from the body end 32, through the body 34 and connecting end 36. The ports 38 can correspond to the fluid conduits 20, such as in number and shape. For example, in certain embodiments, the number of ports 38 in the fluid connector 30 can be the same as the number of fluid conduits 20 in the fluid transport coupling 10. Further, in certain embodiments, the ports 38 can have a circumference matching the inner or outer diameter of the corresponding fluid conduit 20. Furthermore, the port 38 can make a watertight fluid connection with the corresponding fluid conduit 20.

In certain embodiments, as mentioned previously, the ports 38 can be arranged such that the fluid conduits 20 are separated from each other. For example, a portion of the ports 38 can be distributed evenly and circumferentially forming a ring near an outer edge of the surface of the ends while remaining ports are distributed near the center of the end surfaces.

Further, the ports 38 can be arranged such that when the fluid conduits 20 are disposed in the fluid connector, the fluid conduits 20 can be arranged and secured in a spaced relationship. The term "spaced relationship" refers to an arrangement where the ends of the fluid conduits inserted into the fluid connector are not in contact with each other. Furthermore, the ports 38 can be configured such that, when the proximal ends of the fluid conduits 20 are inserted into their corresponding ports 38, the fluid conduits 20 can extend away from the support element to their distal ends 22 in the same axial direction relative to the fluid connector 30.

In certain embodiment, the body end 32 and the connecting end 36 are on opposite sides of the fluid connector 30. For example, the connecting end 36 can refer to the end of the fluid connector 30 furthest from the distal end 22 of the fluid conduits 20, whereas the body end can refer to the end of the fluid connector 30 nearest the distal end 22 of the conduits 20, when the fluid transport coupling 10 is assembled and the fluid conduits 20 are extending in a single axial direction from the fluid connector 30.

The opposing body and connecting ends 32, 36 of the can have essentially the same or different shape, such as an arcuate shape, a polygonal, or an amorphous shape. In particular embodiments, the arcuate shape can include a circle or an ellipse where the eccentricity is greater than 0. In more particular embodiments, the polygonal shape can include a triangle, a square, a pentagon, a hexagon, or a polygon having 7 or more sides. In more particular embodiments, the opposing body and connecting ends 32, 36 of the fluid connector can have a circular shape, as illustrated in FIGS. 1 to 4.

The body 34 can include a sidewall extend a distance D between the body end 32 and the connecting end 36. In certain embodiments, the distance D can be at least 0.62 cm. In further embodiments, the distance D may be no greater than 2.6 cm.

The sidewall of the body 34 can have a perimeter having a shape corresponding to the shape of the ends, particularly the body end 32. For example, as illustrated in FIG. 1, the sidewall can have the shape of a cylinder corresponding to the circular body end 32. In certain embodiments, the diameter of the body can be at least 1.5 cm. In further embodiments, the diameter of the body may be no greater than 4 cm.

In certain embodiments, the connecting end 36 can define a fitting. For example, a fitting can refer to a structure adapted to form a fluid connection with another fluid component. A fitting can include, but is not limited to, a connector, such as a barbed sterile connector, over-molded connection, barbed filters, barbed valve fitting, vessels, bag ports, silicone molded sample bulbs. The fluid component can include a second fluid conduit, a fluid container, or an isolated environment. For example, in particular embodiments, the fitting can be attached to a bioreactor or other equipment for the pharmaceutical or life sciences industries. On the opposite end, the conduits 20 can be adapted to be coupled to a fluid container such as a multi-port bag, carboy, bottle, spinner flask, or seed vials The fluid connection can be adapted to transport fluid to, from, or between the equipment and the fluid container.

The fitting can comprise a flange, such as a flange extending radially outward, such as the flange formed by the connecting end diameter extending beyond the sidewall such that a portion of the connecting end 36 extends radially beyond the perimeter of the body 34, forming an external ridge at the connecting end 36 of the fluid transport coupling 10. In certain embodiments, the connecting end 36 can have a diameter of at least 1 cm, at least 1.4 cm, at least 1.8 cm, or at least 2.2 cm. In further embodiments, the connecting end 36 can have a diameter of no greater than 16 cm, no greater than 15 cm, no greater than 14 cm, or no greater than 13 cm.

As discussed above, the fluid connector 30 can be a composite including a support element 40 and a connector element 50. The connector element 50 can be disposed about the support element 40, and a portion of each of the fluid conduits 20, to form the fluid connector 30, such as overmolded onto the fluid conduits 20. In certain embodiments, the support element 40 can function as a spacer securing and maintaining the fluid conduits 20 in the spaced relationship discussed above, including before, during, or after overmolding the connector element 50 onto the support element 40.

In certain embodiments, the support element 40 can have a diameter of at least 1 cm, at least 1.4 cm, at least 1.8 cm, or at least 2.2 cm. In further embodiments, the support element 40 can have a diameter of no greater than 16 cm, no greater than 15 cm, no greater than 14 cm, or no greater than 13 cm. In certain embodiments, the support element 40 can have a length of at least 0.2 cm, at least 0.3 cm, at least 0.4 cm, or at least 0.5 cm. In further embodiments, the support element 40 can have a length of no greater than 8 cm, no greater than 7 cm, no greater than 6 cm, no greater than 5 cm, or no greater than 4 cm.

In certain embodiments, the support element 40 can include a flexible material comprising a polymer, such as an elastomeric polymer. In particular embodiments, the elastomeric polymer can comprise an ether, an olefin, a vinyl, a polyurethane, an acrylate, a vinyl alcohol, an ethylene copolymer, an ester, a silicone, a fluoropolymer, or any combination thereof. In a more particular embodiment, the support element 40 can include an elastomeric polymer comprising a silicone.

In further embodiments, the support element 40 can be composed of the same material as the fluid conduits 20 or as at least one of the fluid conduits 20. In further embodiments, the support element 50 can be composed of a different material than at least one of the fluid conduits 20 or each of the fluid conduits 20. In particular embodiments where the support element 40 is composed of a different material, the different material can be a more rigid material. The stiffness of the materials can be measured according to ASTM D1043-10.

In certain embodiments, the connector element 50 can be composed of a material essentially the same as or different than the support element 40 or the fluid conduits 20. In particular embodiments, the connector element 50 can include a flexible material comprising a polymer, such as an elastomeric polymer. In particular embodiments, the elastomeric polymer can comprise an ether, an olefin, a vinyl, a polyurethane, an acrylate, a vinyl alcohol, an ethylene copolymer, an ester, a silicone, a fluoropolymer, or any combination thereof. In a more particular embodiment, the connector element 50 can include an elastomeric polymer comprising a silicone.

In certain embodiments, the fluid conduits 20, the support element 40, and the connector element 50 can be composed of compatible materials. For example, the fluid conduits 20, the support element 40, and the connector element 50 can be composed of materials that can form an attachment with each other when the overmolded connector element 50 is formed. In certain embodiments, the overmolded connector element 50 can be mechanically attached the support element 40 and one or more of the fluid conduits 20, such as by adhesion or electrostatic interaction. In further embodiments, the overmolded connector element 50 can be covalently attached or bonded to the support element 40, one or more of the fluid conduits 20, such as each of the fluid conduits 20, or both. As used herein, the term "covalently attached" or "covalently bonded" refers to the forming of a chemical bond that is characterized by the sharing of pairs of electrons between atoms. For example, a covalently attached overmolded connector element 50 can refer to an overmolded connector element 50 that forms chemical bonds with one or more of the fluid conduits 20, as compared to attachment to the fluid conduits 20 via other means, for example, adhesion or electrostatic interaction. It will be appreciated that polymers that are attached covalently to a surface can also be bonded via means in addition to covalent attachment, such as by adhesion and electrostatic interaction.

In further embodiments, fluid transport coupling 10 can be coupled to a fluid component having fluid connection capabilities. It is to be understood that the fluid component can include a single fluid conduit 20, or in other embodiments, can include a plurality of fluid conduits 20. In certain embodiments, the second fluid component can include a fluid conduit, a vessel, or any other structure to which a fluid connection is desired. In particular embodiments, the vessel can include a rigid vessel, such as a drum, a carboy, a tank; a flexible vessel such as a storage bag, a mixing bag, or an isolation bag; or a combination thereof.

The fluid component can have a distal end and a proximal end. The proximal end of the fluid component can be adapted to couple with the proximal end 24 of the fluid conduits 20. In certain embodiments, the overmolded connector element 50 can be covalently bonded to the fluid component. In very particular embodiments, the vessel can include a flexible bag and the overmolded connector element 50 can be covalently bonded to the vessel.

Another aspect of the present disclosure is directed to a method of forming a fluid transport coupling 10. The method can include providing a plurality of fluid conduits 20; and overmolding an overmolded connector element 50 about the plurality of fluid conduits 20 to form a body 34 and a fitting 36.

In particular embodiments, the method can further include providing the support element 40, and engaging the fluid conduits 20 with the support element 40. When engaged, the fluid conduits 20 can form a spaced relationship with one another such that when overmolded, the overmolding material can surround the support element 40 and each of the fluid conduits 20.

As discussed above, it is a particular advantage of the fluid transport coupling 10 and method of making a fluid transport coupling 10 that a sanitary, watertight fluid connection can be made between a plurality of fluid conduits 20 and a separate fluid component via a fluid connector where the plurality of fluid conduits 20 and the fluid connector are joined simultaneously using the overmolded element. The ovemolded fluid connector can provide a single sanitary fluid connection that provides options for multiple outlets or inlets without having to connect each port individually. In addition, the overmolded fluid connector can provide a single material construction and, thus, does not include seams, which are vulnerable to leaking.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the embodiments as listed below.

Embodiment 1

A sanitary fluid transport coupling comprising:
a plurality of fluid conduits, each fluid conduit having a distal end and a proximal end; and a connector element disposed about and securing the plurality of fluid conduits at the proximal ends, wherein the connector element is an overmolded connector element defining a fitting that forms or is adapted to form a fluid connection with another fluid conduit, fluid container, or isolated environment.

Embodiment 2

A sanitary fluid transport coupling comprising:
a plurality of fluid conduits, each fluid conduit having a distal end and a proximal end;
a support element adapted to secure a spaced relationship between the plurality of second conduits at the distal end of the plurality of fluid conduits; and
a connector element disposed adjacent the support element,
wherein the connector element is an overmolded connector element defining a fitting that is adapted to form a fluid connection with another fluid conduit, fluid container, or isolated environment.

Embodiment 3

A method of forming a sanitary fluid transport coupling, the method comprising:
providing a plurality of fluid conduits having an inner bore;
providing a mold comprising a plurality of protrusions adapted to fit within the inner bores of the plurality of fluid conduits; and
overmolding a composition to form an connector element about the support element, wherein the overmolded connector element defines a fitting that forms or is adapted to form a fluid connection with another fluid conduit, fluid container, or an other isolated environment.

Embodiment 4

A method of forming a sanitary fluid transport coupling, the method comprising:
providing a plurality of fluid conduits in a spaced relationship via a support element; and
forming an connector element via overmolding about the support element,
wherein the overmolded connector element defines a fitting that forms or is adapted to form a fluid connection with another fluid conduit, fluid container, or an other isolated environment.

Embodiment 5

The method of any one of embodiments 3 and 4, wherein providing a plurality of fluid conduits in a spaced relationship via a support element comprises providing a support element comprising a plurality of apertures, and inserting each of the plurality of fluid conduits into the plurality of apertures.

Embodiment 6

The coupling or method of any one of embodiments 3 to 5, wherein one or more of the plurality of fluid conduits are flexible.

Embodiment 7

The coupling or method of any one of the preceding embodiments, wherein one or more of the plurality of fluid conduits comprise a polymer, such as an elastomeric polymer, such as an elastomeric polymer comprising an ether, an olefin, a vinyl, a polyurethane, an acrylate, a vinyl alcohol, an ethylene copolymer, an ester, a silicone, a fluoropolymer, or any combination thereof.

Embodiment 8

The coupling or method of any one of the preceding embodiments, wherein one or more of the plurality of fluid conduits comprises a silicone.

Embodiment 9

The coupling or method of any one of the preceding embodiments, wherein the plurality of fluid conduits comprises at least 2, at least 3, at least 4, at least 5, at least 6, at least 7, at least 8, at least 9, or even at least 10 distinct fluid conduits.

Embodiment 10

The coupling or method of any one of the preceding embodiments, wherein the plurality of fluid conduits comprises no greater than 15, no greater than 14, no greater than 13, no greater than 12, no greater than 11, or even no greater than 10 distinct fluid conduits.

Embodiment 11

The coupling or method of any one of the preceding embodiments, wherein the plurality of fluid conduits comprises a number of distinct fluid conduits in a range of 2 to 15, 5 to 14, or even 7 to 13 distinct fluid conduits.

Embodiment 12

The coupling or method of any one of the preceding embodiments, wherein each of the plurality of the fluid conduits have essentially the same inner diameter.

Embodiment 13

The coupling or method of any one of the preceding embodiments, wherein each of the plurality of the fluid conduits have essentially the same outer diameter.

Embodiment 14

The coupling or method of any one of the preceding embodiments, wherein at least two of the plurality of the fluid conduits have a different inner diameter.

Embodiment 15

The coupling or method of any one of the preceding embodiments, wherein at least two of the plurality of the fluid conduits have a different outer diameter.

Embodiment 16

The coupling or method of any one of the preceding embodiments, wherein the connector element comprises a polymer, such as an elastomeric polymer, such as an elastomeric polymer comprising an ether, an olefin, a vinyl, a polyurethane, an acrylate, a vinyl alcohol, an ethylene copolymer, an ester, a silicone, a fluoropolymer, or any combination thereof.

Embodiment 17

The coupling or method of any one of the preceding embodiments, wherein the connector element comprises a silicone.

Embodiment 18

The coupling or method of any one of the preceding embodiments, wherein the support element comprises a polymeric material.

Embodiment 19

The coupling or method of any one of the preceding embodiments, wherein the support element comprise a polymeric material comprising a polymer, such as an elastomeric polymer, such as an elastomeric polymer comprising an ether, an olefin, a vinyl, a polyurethane, an acrylate, a vinyl alcohol, an ethylene copolymer, an ester, a silicone, a fluoropolymer, or any combination thereof.

Embodiment 20

The coupling or method of any one of the preceding embodiments, wherein the support element comprises a silicone.

Embodiment 21

The coupling or method of any one of the preceding embodiments, wherein the support element has a greater rigidity than one or more of the plurality of fluid conduits.

Embodiment 22

The coupling or method of any one of the preceding embodiments, wherein the support element has a greater rigidity than the connector element.

Embodiment 23

The coupling or method of any one of the preceding embodiments, wherein the connector element has a greater rigidity than one or more of the plurality of fluid conduits.

Embodiment 24

The coupling or method of any one of the preceding embodiments, wherein the connector element is covalently bonded to the support element.

Embodiment 25

The coupling or method of any one of the preceding embodiments, wherein one or more of the plurality of fluid conduits is covalently bonded to the support element.

Embodiment 26

The coupling or method of any one of the preceding embodiments, wherein the plurality of fluid conduits are covalently bonded to the support element.

Embodiment 27

The coupling or method of any one of the preceding embodiments, wherein one or more of the plurality of fluid conduits is covalently bonded to the connector element.

Embodiment 28

The coupling or method of any one of the preceding embodiments, wherein each of the plurality of fluid conduits are covalently bonded to the connector element.

Embodiment 29

The coupling or method of any one of the preceding embodiments, wherein one or more of the plurality of fluid conduits, the support element, and the connector element are covalently bonded to each other.

Embodiment 30

The coupling or method of any one of the preceding embodiments, wherein each the plurality of fluid conduits, the support element, and the connector element are covalently bonded to each other.

Embodiment 31

The coupling or method of any one of the preceding embodiments, wherein the connector element is composed of essentially the same material as the support element.

Embodiment 32

The coupling or method of any one of the preceding embodiments, wherein one or more of the plurality of fluid conduits is composed of essentially the same material as the support element.

Embodiment 33

The coupling or method of any one of the preceding embodiments, wherein each of the plurality of fluid conduits are composed of essentially the same material as the support element.

Embodiment 34

The coupling or method of any one of the preceding embodiments, wherein one or more of the plurality of fluid conduits is composed of essentially the same material as the connector element.

Embodiment 35

The coupling or method of any one of the preceding embodiments, wherein each of the plurality of fluid conduits are composed of essentially the same material as the connector element.

Embodiment 36

The coupling or method of any one of the preceding embodiments, wherein one or more of the plurality of fluid conduits, the support element, and the connector element are composed of essentially the same material.

Embodiment 37

The coupling or method of any one of the preceding embodiments, wherein the plurality of fluid conduits, the support element, and the connector element are composed of essentially the same material.

Embodiment 38

The coupling or method of any one of the preceding embodiments, wherein the connector element comprises a body and a fitting.

Embodiment 39

The coupling or method of any one of the preceding embodiments, wherein the connector element comprises a fitting, wherein the fitting is adapted to couple with and form a fluid connection with another fluid conduit, fluid container, or isolated environment.

Embodiment 40

The coupling or method of any one of the preceding embodiments, wherein the connector element comprises a fitting comprising a flange.

Embodiment 41

The coupling or method of any one of the preceding embodiments, wherein the connector element comprises a body and a fitting comprising a flange extending radially outwardly from the body.

Embodiment 42

An assembly comprising the sanitary fluid transport coupling of any one of the preceding embodiments coupled to a vessel and a second component in fluid communication with the plurality of fluid conduits.

Embodiment 43

The assembly of embodiment 42, wherein the second component comprises a fluid conduit, a vessel, or any other structure to which a fluid connection is desired.

Embodiment 44

The assembly of any one of embodiments 42 and 43, wherein the second component comprises a fluid conduit.

Embodiment 45

The assembly of any one of embodiments 42 to 44, wherein the second component comprises a vessel.

Embodiment 46

The assembly of any one of embodiments 42 to 45, wherein the connector element is covalently bonded to the second component.

Embodiment 47

The assembly of any one of embodiments 42 to 46, wherein the vessel comprises: a rigid vessel such as a drum, a carboy, a tank; a flexible vessel such as a storage bag, a mixing bag, or an isolation bag; or a combination thereof.

Embodiment 48

The assembly of any one of embodiments 42 to 47, wherein the vessel comprises a flexible bag, and wherein the overmolded element is covalently bonded to the vessel.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A sanitary fluid transport coupling comprising:
a plurality of fluid conduits, each fluid conduit consisting of a distal end, a proximal end, and a length extending from the distal end to the proximal end, wherein at least one of the plurality of fluid conduits comprises an enclosed tube along the entirety of its length; and
a fluid connector comprising a body end, and a connecting end, wherein the fluid connector is overmolded to secure the plurality of fluid conduits at the proximal ends of the plurality of fluid conduits, wherein the connecting end of the fluid connector comprises a fitting that forms or is adapted to form a fluid connection with another fluid conduit, fluid container, or isolated environment, wherein the body end of the fluid connector consists of a substantially flat circular surface without axial projections, and at least one port in the circular surface extending from the body end to the connecting end, wherein the at least one port makes a watertight fluid connection with a corresponding fluid conduit, wherein the fitting comprises an axial flange tapering to an outermost axial edge of the fluid transport coupling, and
wherein the connecting end is overmolded onto a circular support element and the circular support element is configured to arrange and secure a spaced relationship between the plurality of fluid conduits.

2. The coupling of claim 1, wherein one or more of the plurality of fluid conduits comprise a polymer.

3. The coupling of claim 1, wherein one or more of the plurality of fluid conduits comprises a silicone.

4. The coupling of claim 1, wherein the fluid connector comprises a polymer.

5. The coupling of claim 1, wherein the fluid connector comprises a silicone.

6. The coupling of claim 1, wherein the plurality of fluid conduits comprises no greater than 15 distinct fluid conduits.

7. The coupling of claim 1, wherein the plurality of fluid conduits comprises a number of distinct fluid conduits in a range of 5 to 15 distinct fluid conduits.

8. The coupling of claim 1, wherein at least two of the plurality of the fluid conduits have a different inner diameter.

9. The coupling of claim 1, wherein at least two of the plurality of the fluid conduits have a different outer diameter.

10. The coupling of claim 1, wherein each of the plurality of the fluid conduits have the same inner diameter.

11. The coupling of claim 1, wherein each of the plurality of the fluid conduits have the same outer diameter.

12. The coupling of claim 1, wherein a ridge of the axial flange comprises a step.

13. The coupling of claim 1, wherein one or more of the plurality of fluid conduits consists of an ether, an olefin, a vinyl, a polyurethane, an acrylate, a vinyl alcohol, an ethylene copolymer, an ester, a silicone, a fluoropolymer, or any combination thereof.

14. The coupling of claim 1, wherein the fluid connector consists of an ether, an olefin, a vinyl, a polyurethane, an acrylate, a vinyl alcohol, an ethylene copolymer, an ester, a silicone, a fluoropolymer, or any combination thereof.

15. The coupling of claim 1, wherein the support element consists of an ether, an olefin, a vinyl, a polyurethane, an acrylate, a vinyl alcohol, an ethylene copolymer, an ester, a silicone, a fluoropolymer, or any combination thereof.

16. The coupling of claim 1, wherein the connector element consists of an ether, an olefin, a vinyl, a polyurethane, an acrylate, a vinyl alcohol, an ethylene copolymer, an ester, a silicone, a fluoropolymer, or any combination thereof.

17. A sanitary fluid transport coupling comprising:
a plurality of fluid conduits, each fluid conduit consisting of a distal end, a proximal end, and a length extending from the distal end to the proximal end; and
a fluid connector overmolded to secure the plurality of fluid conduits at the proximal ends, wherein the fluid connector defines a fitting that is adapted to form a fluid connection with another fluid component, fluid container, or isolated environment, wherein the fluid connector comprises a body end and a connecting end, wherein the body end of the fluid connector consists of a substantially flat circular surface without axial projections, and a plurality of ports in the circular surface extending from the body end to the connecting end, wherein at least one port of the plurality of ports makes a watertight fluid connection with a corresponding fluid conduit, wherein the fitting comprises an axial flange at an outermost axial edge of the connecting end and at an outermost axial edge of the fluid transport coupling, and wherein the connecting end is overmolded onto a circular support element and the circular support element is configured to arrange and secure a spaced relationship between the plurality of fluid conduits.

18. The coupling of claim 17, wherein the fluid connector comprise a polymeric material comprising a polymer.

19. The coupling of claim 17, wherein one or more of the plurality of fluid conduits and the fluid connector are composed of the same material that consists of at least one of a silicone or a thermoplastic elastomer.

20. The coupling of claim 17, wherein the fluid connector has a greater rigidity than one or more of the plurality of fluid conduits.

21. The coupling of claim 17, wherein the fluid connector has a greater rigidity than one or more of the plurality of fluid conduits.

22. The coupling of claim 17, wherein at least one of the plurality of ports has a circumference matching an inner or an outer diameter of the corresponding fluid conduit.

* * * * *